United States Patent
Bushmaker et al.

(10) Patent No.: US 8,716,685 B1
(45) Date of Patent: May 6, 2014

(54) SYSTEMS AND METHODS FOR USE IN GENERATING PULSED TERAHERTZ RADIATION

(71) Applicant: The Aerospace Corporation, El Segundo, CA (US)

(72) Inventors: Adam Wayne Bushmaker, Los Angeles, CA (US); William T. Lotshaw, Rancho Palos Verdes, CA (US)

(73) Assignee: The Aerospace Corporation, El Segundo, CA (US)

( * ) Notice: Subject to any disclaimer, the term of this patent is extended or adjusted under 35 U.S.C. 154(b) by 0 days.

(21) Appl. No.: 13/728,688

(22) Filed: Dec. 27, 2012

(51) Int. Cl.
  *H01S 5/00* (2006.01)
  *H01S 3/00* (2006.01)

(52) U.S. Cl.
  CPC ............. *H01S 5/0057* (2013.01); *H01S 3/0057* (2013.01)
  USPC ..................................................... 250/504 R

(58) Field of Classification Search
  USPC ................................ 250/493.1, 504.1, 504 R
  See application file for complete search history.

(56) References Cited

U.S. PATENT DOCUMENTS

| | | | |
|---|---|---|---|
| 5,862,287 A | 1/1999 | Stock et al. | |
| 6,249,630 B1 | 6/2001 | Stock et al. | |
| 7,095,772 B1 | 8/2006 | Delfyett et al. | |
| 7,272,158 B1 | 9/2007 | Hayes et al. | |
| 7,558,302 B1 | 7/2009 | Delfyett et al. | |
| 8,564,875 B2 * | 10/2013 | Kawada et al. | ............... 359/326 |
| 2005/0242287 A1 | 11/2005 | Hakimi | |
| 2008/0023633 A1 | 1/2008 | Mittleman et al. | |
| 2009/0213880 A1 | 8/2009 | Ouchi et al. | |
| 2009/0296749 A1 | 12/2009 | Sucha et al. | |
| 2011/0210252 A1 * | 9/2011 | Ouchi et al. | ............... 250/338.1 |
| 2012/0032081 A1 | 2/2012 | Itsuji | |

OTHER PUBLICATIONS

Goda et al. 'Hybrid Dispersion Laser Scanner', Jun. 8, 2012, Scientific Reports, 2:445.*
Jepsen et al., Generation and Detection of Terahertz Pulses from Biased Semiconductor Antennas, J. Opt. Soc. Am. B, vol. 13, No. 11, Nov. 1996.
Suen et al., Characterization and Modeling of a Terahertz Photoconductive Switch, Applied Physics Letters 96, Department of Electrical and Computer Engineering, University of California, Santa Barbara, California, Apr. 5, 2010.

(Continued)

*Primary Examiner* — Nicole Ippolito
*Assistant Examiner* — Eliza Osenbaugh-Stewart
(74) *Attorney, Agent, or Firm* — Duane Morris LLP; Manita Rawat

(57) ABSTRACT

A terahertz generating assembly generally includes a light emitting device that is configured to generate at least one pulsed light beam. A first dispersion member is positioned proximate to the light emitting device, wherein the first dispersion member is configured to facilitate a temporal dispersion of the light beam. A second dispersion member is positioned proximate to the first dispersion member and to the light emitting device, wherein the second dispersion member is configured to facilitate a spatial dispersion of the light beam. A lens is positioned proximate to each of the first and second dispersion members, wherein the lens is configured to focus the temporal and spatial dispersions to produce at least one moving spot of light. At least one waveguide is positioned proximate to the lens, wherein the waveguide is configured to apply a biased voltage to the spot of light to generate pulsed terahertz radiation.

21 Claims, 2 Drawing Sheets

(56) References Cited

OTHER PUBLICATIONS

Weling et al., Generation of Tunable Narrowband THz Radiation from Large Aperture Photoconducting Antennas, Applied Physics Letter 64, American Institute of Physics, 1994.

Matsuura et al., A Traveling-Wave THz Photomixer Based on Angle-Tuned Phase Matching, Applied Physics Letters, vol. 74, No. 19, May 10, 1999.

Barrientos et al, Vertically Illuminated TW-UTC Photodiodes for Terahertz Generation; 21st International Symposium on Space Terahertz Technology, Oxford, Mar. 23-25, 2010.

Grischkowsky et al, Far-Infrared Time-Domain Spectroscopy with Terahertz Beams of Dielectrics and Semiconductors, J. Opt. Soc. Am., B/vol. 7, No. 10, Oct. 1990.

Harper et al, Control of Terahertz Pulse Generation by Optical Pulse Shaping, IEEE Cardiff 2-9, 2007.

Jarrahi et al, High Power Tunable Terahertz Generation Based on Photoconductive Antenna Arrays, SMIRC Lab, Stanford University, Stanford, CA, IEEE 2008.

Brown, E.R., Advancements in Photomixing and Photoconductive Switching for THz Spectroscopy and Imaging, Wright State University, Dayton, OH, 2011.

Orfanidis, S.J., Electromagnetic Waves and Antennas, Rutgers University, Piscataway, NJ, 2008.

Nikoghosyan et al, Terahertz Radiation Generation in Waveguide Partially Filled with Nonlinear Crystal, 33rd International Conference on Infrared, Millimeter and Terahertz Waves, Sep. 15-19, 2008.

* cited by examiner

SYSTEMS AND METHODS FOR USE IN GENERATING PULSED TERAHERTZ RADIATION

BACKGROUND

The field of the invention relates generally to systems that generate electromagnetic waves and, more particularly, to systems and methods for use in generating pulsed terahertz radiation.

Terahertz radiation or terahertz waves include electromagnetic waves at frequencies in the range of about 0.3 terahertz to about 3.0 terahertz. There are at least some known applications for terahertz radiation in the civil, defense, and commercial markets. For example, terahertz radiation is able to penetrate into fabrics and plastics and is, therefore, used in surveillance technologies and methods. Terahertz radiation may also be used for the evaluation of materials, rockets, and satellite structural components.

Gyrotrons and backward wave oscillators are known sources for generating terahertz radiation. However, such systems are limited as reliable sources for terahertz radiation. For example, these known sources, for generating terahertz radiation, have a limited or substantially low power output capability. For example, in using terahertz range modulation for satellite communication, the atmosphere may absorb some of the terahertz waves, requiring additional input power for generating a greater power output to overcome such attenuations. Moreover, at least some known sources for terahertz radiation are unable to shape the pulse of the terahertz radiation. Accordingly, it may be difficult to perform, for example, a controlled chemical reaction using terahertz radiation. As such, the generation of terahertz radiation using known systems and methods is not efficient and does not provide for varying applicability.

BRIEF DESCRIPTION

In one embodiment, a terahertz generating assembly is provided. The terahertz generating assembly generally includes a light emitting device that is configured to generate at least one pulsed light beam. A first dispersion member is positioned proximate to the light emitting device, wherein the first dispersion member is configured to facilitate a temporal dispersion of the pulsed light beam. A second dispersion member is positioned proximate to the first dispersion member and to the light emitting device, wherein the second dispersion member is configured to facilitate a spatial dispersion of the pulsed light beam. A lens is positioned proximate to each of the first and second dispersion members, wherein the lens is configured to focus the temporal and spatial dispersions of the pulsed light beam to produce at least one moving spot of light. At least one waveguide is positioned proximate to the lens, wherein the waveguide is configured to apply a biased voltage to the moving spot of light to generate pulsed terahertz radiation.

In another embodiment, a system is provided. The system includes an antenna and a terahertz generating assembly coupled to the antenna. The terahertz generating assembly includes a light emitting device that is configured to generate at least one pulsed light beam. A first dispersion member is positioned proximate to the light emitting device, wherein the first dispersion member is configured to facilitate a temporal dispersion of the pulsed light beam. A second dispersion member is positioned proximate to the first dispersion member and to the light emitting device, wherein the second dispersion member is configured to facilitate a spatial dispersion of the pulsed light beam. A lens is positioned proximate to each of the first and second dispersion members, wherein the lens is configured to focus the temporal and spatial dispersions of the pulsed light beam to produce at least one moving spot of light. At least one waveguide is positioned proximate to the lens, wherein the waveguide is configured to apply a biased voltage to the moving spot of light to generate pulsed terahertz radiation.

In yet another embodiment, a method of generating pulsed terahertz radiation is provided. At least one pulsed light beam is generated via a light emitting device. A temporal dispersion of the pulsed light beam is provided via a first dispersion member that is positioned proximate to the light emitting device. A spatial dispersion of the pulsed light beam is provided via a second dispersion member that is positioned proximate to the first dispersion member and to the light emitting device. The temporal and spatial dispersions of the pulsed light beam are focused, via a lens positioned proximate to each of the first and second dispersion members, to produce at least one moving spot of light. A biased voltage is applied to the moving spot of light, via a first waveguide that is positioned proximate to the lens, to generate pulsed terahertz radiation.

DETAILED DESCRIPTION

The exemplary apparatus, systems, and methods described herein provide an efficient solution to generating pulsed terahertz radiation, wherein the pulse shape of the terahertz radiation may also be controlled. More specifically, the embodiments described herein provide a terahertz generating assembly that uses a combination of a temporal and spatial dispersion of at least one pulsed light beam to create at least one moving spot of light, wherein a biased voltage can be applied to the moving spot of light to generate pulsed terahertz radiation. The terahertz generating assembly also includes capabilities for frequency and waveform agility. Accordingly, the terahertz generating assembly is a reliable source for terahertz radiation that may be used in various systems.

Figure 1:
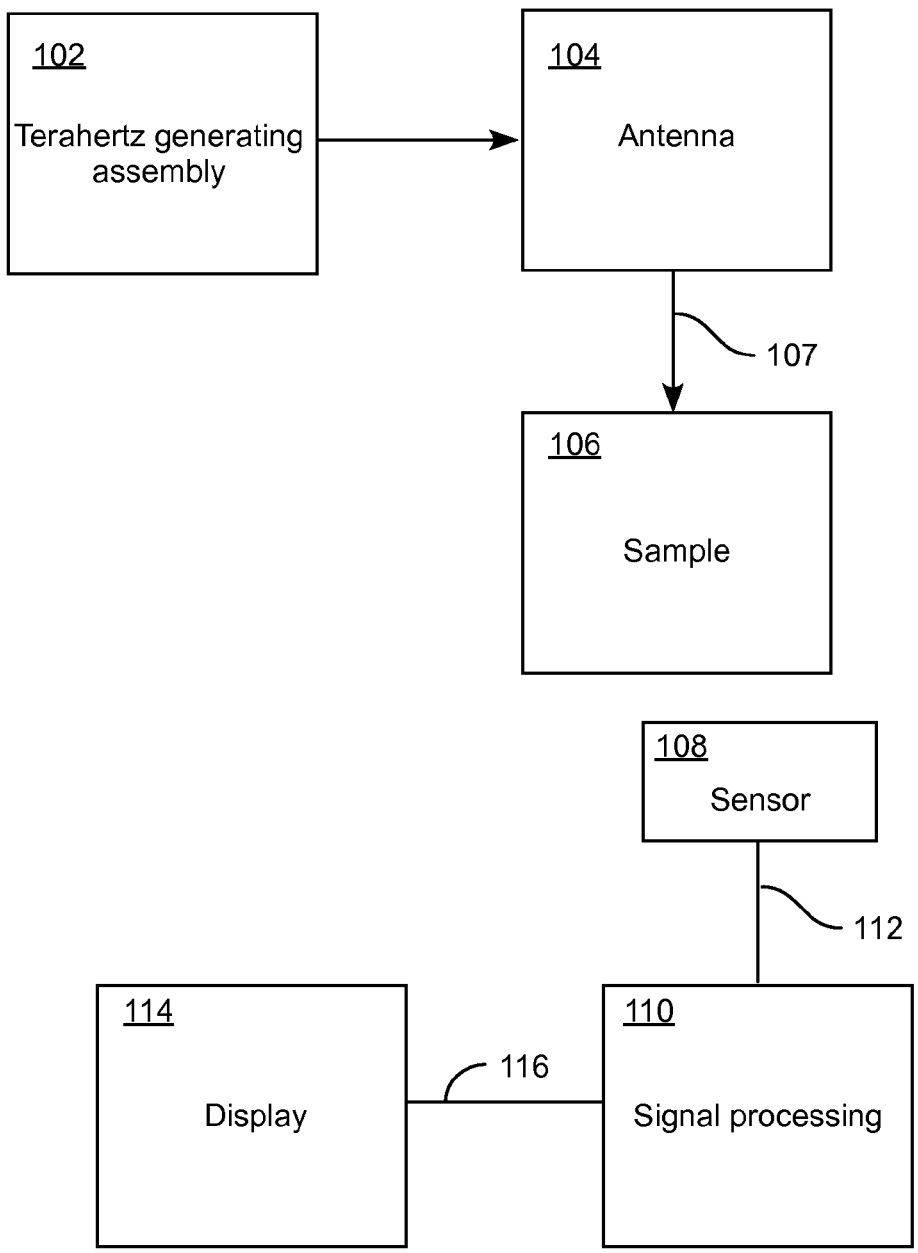
FIG. 1 is block diagram of an exemplary system.

FIG. 1 illustrates an exemplary system 100. In the exemplary embodiment, system 100 is a spectroscopy system that is configured to facilitate the characterization of a component or a chemical reaction. Although the exemplary embodiment illustrates a spectroscopy system, the present disclosure is not limited to spectroscopy systems and one of ordinary skill in the art will appreciate that the current disclosure may be used in connection with any type of system, such as, for example, a satellite communication system.

System 100 includes a terahertz generating assembly 102 that is coupled to an antenna 104. In the exemplary embodiment, terahertz generating assembly 102 is configured to generate terahertz radiation (i.e., electromagnetic waves at frequencies in the range of about 0.3 terahertz to about 3.0 terahertz). Moreover, while only one antenna 104 is illustrated in FIG. 1, system 100 may include a plurality of antennas 104 that are each coupled to assembly 102 at various locations. It should be noted that, as used herein, the term "couple" is not limited to a direct mechanical and/or an electrical connection between components, but may also include an indirect mechanical and/or electrical connection between multiple components.

In the exemplary embodiment, a sample 106 that is being tested or evaluated, such as a satellite structural component or material, is positioned proximate to antenna 104 such that terahertz waves may be propagated from antenna 104 to sample 106, as shown by arrow 107. At least one transducer or sensor 108 is positioned proximate to sample 106, wherein sensor 108 is configured to detect various parameters related to sample 106. For example, sensor 108 may be configured to detect the energy being absorbed by sample 106 after the terahertz waves are directed at sample 108.

A signal processing device 110 is coupled to sensor 108 via a data conduit 112. Alternatively, signal processing device 110 may be wirelessly coupled to sensor 108. In the exemplary embodiment, signal processing device 110 is configured to receive at least one signal that is representative of the energy absorption by sample 106 from sensor 108. Signal processing device 110 is configured to process and/or analyze the signal(s) received from sensor 108. As used herein, the term "process" refers to performing an operation on, adjusting, filtering, buffering, and/or altering at least one characteristic of a signal. For example, signal processing device 110 may be a computing device that includes a circuit (not shown) or a processor (not shown) such that signal processing device 110 can be configured to utilize either analog or digital signal processing techniques as well as using a hybrid mix of the two to generate an output that is representative of the signal(s) received from sensor 108.

A display device 114 is coupled to signal processing device 110 via a data conduit 116. In the exemplary embodiment, display device 114 is configured to display the output(s) generated by signal processing device 110 to a user. For example, display device 114 may be a visual display device, such as a cathode ray tube (CRT), a liquid crystal display (LCD), an light emitting diode (LED) display, an organic LED display, and/or an "electronic ink" display. Alternatively, display device 114 may be an audio output device that includes an audio adapter and/or a speaker.

During operation, terahertz generating assembly 102 first generates terahertz radiation. As explained in more detail below, assembly 102 enables a temporal and spatial dispersion of a pulsed light beam, wherein the dispersions are focused to produce at least one moving spot of light to generate pulsed terahertz radiation. The pulsed terahertz radiation is channeled to antenna 104 such that the terahertz waves can be propagated onto sample 106. Sensor 108 detects the energy being absorbed by sample 106 and sensor 108 transmits at least one signal representative of the detected energy absorption to signal processing device 110 via conduit 112. Signal processing device 110 analyzes the signal(s) and an output is generated that can be displayed to a user via display device 114.

Figure 2:
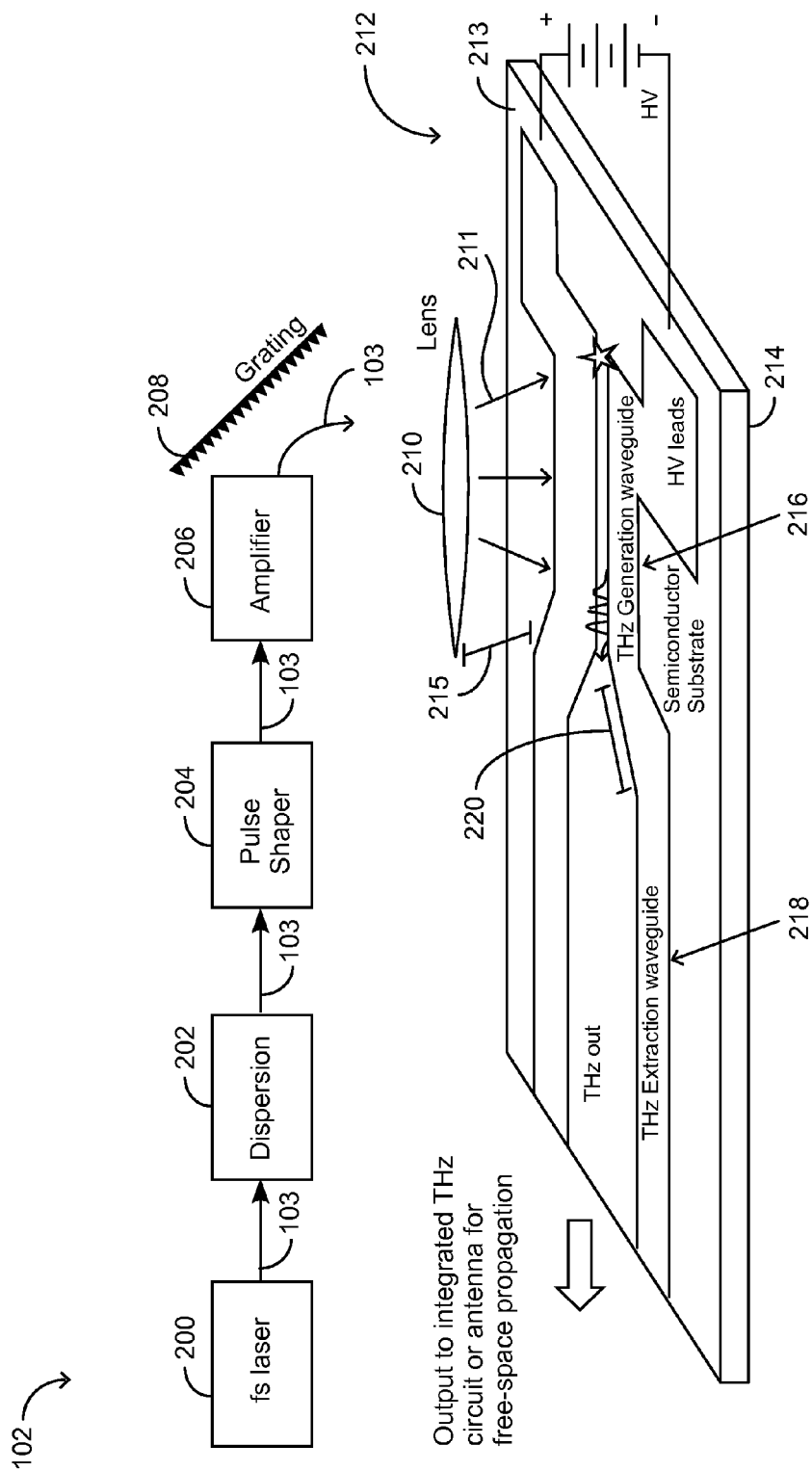
FIG. 2 is a block diagram of an exemplary terahertz generating assembly that may be used with the system shown in FIG. 1.

FIG. 2 is a block diagram of terahertz generating assembly 102 (shown in FIG. 1). In the exemplary embodiment, assembly 102 includes a light emitting device 200 that is configured to generate at least one pulsed light beam that is channeled through assembly 102, as shown by arrows 103. Light emitting device 200, in the exemplary embodiment, is a pulsed laser, such as a femtosecond (fs) ultrashort pulsed laser. Alternatively, light emitting device 200 may be any suitable type of laser device or system that enables terahertz generating assembly 102 and/or system 100 (shown in FIG. 1) to function as described herein.

A first dispersion member 202 is positioned proximate to light emitting device 200 such that first dispersion member 202 is enabled to receive pulsed light beams from light emitting device 200. Moreover, first dispersion member 202 is configured to facilitate a temporal dispersion of the pulsed light beam(s) received from light emitting device 200. In the exemplary embodiment, first dispersion member 202 may be a dielectric medium, such as glass or optical fiber. For example, first dispersion member 202 may be a coil of optical fiber. Alternatively, first dispersion member 202 may be any type of medium or component that facilitates a temporal dispersion of light and that enables assembly 102 and/or system 100 to function as described herein.

Assembly 102 may also include a pulse shaper 204 that is positioned proximate to first dispersion member 202 such that pulse shaper 204 may receive the dispersed light beam(s) from first dispersion member 202. In the exemplary embodiment, pulse shaper 204 may be any suitable type of pulse shaper known in the art and includes at least one pulse shaping filter (not shown), such as a trivial boxcar filter, a sinc-shaped filter, raised-cosine filter, and/or a Gaussian filter.

Pulse shaper 204, in the exemplary embodiment, is configured to tune the dispersion generated by first dispersion member 202. More specifically, pulse shaper 204 is configured to control a pulse shape of the dispersed pulsed light beam(s). Pulse shaper 204 may also be configured to change the delay and the attenuation of the wavelength(s) of the dispersed pulsed light beam(s) received from first dispersion member 202. For example, in the exemplary embodiment, the terahertz pulse shape that is generated by assembly 102 may be tuned by changing the laser or beam spot velocity and the laser or beam pulse shape with pulse shaper 204. More specifically, the pulses may be customized for specific performance attributes in various pulsed terahertz applications. Computer optimization algorithms may be used and programmed into, for example, a control system (not shown) that includes a controller (not shown) coupled to pulse shaper 204. Based on the input provided to the control system, the controller may control pulse shaper 204 to optimize various parameters for the terahertz pulse. Such parameters may include, for example, terahertz pulse bandwidth, energy, center frequency, or more complicated metrics, such as a measured response from a molecular excitation.

Terahertz generating assembly 102, in the exemplary embodiment, also includes an amplifier 206 that is positioned proximate to pulse shaper 204. Amplifier 206 is configured to amplify the pulsed light beam(s) such that greater power output may be subsequently generated. More specifically, because of the spatially and temporally de-localized nature of the terahertz generation, amplifier 206 substantially increases the laser or light beam power that results in high power terahertz pulses. In the exemplary embodiment, amplifier 206 may be any type of optical amplifier 206 known in the art, such as a doped-fiber amplifier, bulk laser, or a Raman amplifier. Moreover, terahertz generating assembly 102 includes a second dispersion member 208 that is adjacent to amplifier 206 and positioned proximate to first dispersion member 202 and light emitting device 200. In the exemplary embodiment, second dispersion member 208 may be a prism or a grating that is configured to facilitate a spatial dispersion of the pulsed light beam(s).

A lens 210 is positioned adjacent to second dispersion member 208 and proximate to first dispersion member 202, wherein lens 210 is configured to focus the temporal and spatial dispersions of the pulsed light beam(s) to produce at least one moving spot of light. The moving spot of light is directed onto a substrate member 212 that is positioned proximate to lens 210, as shown by arrows 211. In the exemplary embodiment, substrate member 212 is a substantially rectangular plate that is fabricated from a semiconducting material, such as Gallium Arsenide. While substrate member 212 is substantially rectangular, substrate member 212 may have any suitable shape that enables assembly 102 and/or system 100 to function as described herein. In the exemplary embodiment, substrate member 212 has a first surface 213 and a second surface 214, wherein lens 210 is positioned a predefined distance 215 from first surface 213.

In the exemplary embodiment, at least one waveguide, such as a terahertz generation waveguide 216 and a terahertz extraction waveguide 218, are coupled to substrate member 212. More specifically, in the exemplary embodiment, waveguides 216 and 218 are coupled to substrate member first surface 213 such that waveguide 216 is positioned a predefined distance 220 from waveguide 218. In the exemplary embodiment, terahertz generation waveguide 216 is positioned proximate to lens 210, and terahertz generation waveguide 216 is a rectangular strip waveguide that is configured to apply a biased voltage to the moving spot of light to generate pulsed terahertz radiation. Waveguide 216 is also configured to contain and propagate the terahertz waves that are generated. Terahertz extraction waveguide 218 is a rectangular strip waveguide that is configured to provide a channel or output terminal for the pulsed terahertz radiation such that the terahertz waves may be channeled to antenna 104 (shown in FIG. 1), wherein the waves are propagated onto sample 106 (shown in FIG. 1).

Moreover, in the exemplary embodiment, the bandwidth limiting factor during terahertz generation is the response time of substrate member 212. As such, the pulse duration increase should not adversely affect the terahertz pulse bandwidth, provided the fs pulse is not stretched. The pulse duration is increased proportionately to the square root of the time stretch factor, as shown in Equation 1 below.

$$(\text{fs laser pulse}) \times \text{sqrt}(\text{time stretch factor}) = \text{pulse duration} \qquad \text{Eq. 1}$$

For example, if a 40 fs laser pulse is dispersed such that the total pulse duration is 4 picoseconds (ps) for a time stretch factor of 100, then at any given spot on waveguide 216 and/or waveguide 218, the pulse duration is then 40 fs×sqrt(100) =400 fs. Moreover, the length of waveguides 216 and/or 218 are directly related to a terahertz group velocity ($V_g$), as shown in Equation 2 below.

$$(V_g) \times (\text{total pulse duration}) = \text{waveguide length} \qquad \text{Eq. 2}$$

For example, if the terahertz group velocity in waveguide 216 or waveguide 218 is 0.3 mm/ps, then the waveguide is 0.3 mm/ps×4 ps=1.2 mm long.

During operation, light emitting device 200 generates at least one pulsed light beam that is channeled through first dispersion member 202, wherein the pulsed light beam(s) are temporally dispersed. The pulsed light beam(s) are then passed through pulse shaper 204 and amplifier 206. The pulsed light beam(s) are channeled through second dispersion member 208 such that the light beam(s) are spatially dispersed. More specifically, the different frequencies are deviated by second dispersion member 208 at different angles. Lens 210 focuses the different frequencies to at least one moving spot of light on substrate member 212. More specifically, because of the chirp in the pulse introduced by the dispersions, the different wavelengths in the pulse arrive at substrate member 212 at different times, resulting in a moving spot of light.

Terahertz generation waveguide 216 applies a biased voltage to the moving spot of light to generate terahertz radiation. More specifically, the moving spot of light generates a terahertz pulse though optical rectification, which grows in amplitude through superposition as it travels with the light spot down the terahertz generation waveguide 216. The terahertz pulse can then be coupled from the generation area by terahertz extraction waveguide 216 into integrated circuitry or antenna 104 for propagation.

The speed with which the spot traverses waveguides 216 and 218 can be tailored by second dispersion member 208. For example, the type of grating that is used can impact the speed. Moreover, by changing the focal length of lens 210, the spot speed can be matched with the terahertz group velocity ($V_g$) of terahertz generation waveguide 216. When the pulsed light beam is dispersed via the first and second dispersion members 202 and 208, respectively, the optical bandwidth at each spot on terahertz generation waveguide 216 is substantially reduced. As a result, the on/off time of the laser or light beam pulse at any given spot will be increased.

As compared to known systems that generate terahertz radiation, the above-described system includes a terahertz generating assembly that efficiently generates pulsed terahertz radiation, wherein the pulse shape of the terahertz radiation may be controlled. More specifically, the terahertz generating assembly uses a combination of temporal and spatial dispersions of at least one pulsed light beam to create at least one moving spot of light, wherein a biased voltage can be applied to the moving spot of light to generate pulsed terahertz radiation. The terahertz generating assembly also includes an amplifier that can facilitate greater power output and a pulse shaper that provides capabilities for frequency and waveform agility. Accordingly, the terahertz generating assembly is a reliable source for terahertz radiation that can be used in various systems and applications.

Exemplary embodiments of the apparatus, systems, and methods are described above in detail. The apparatus, systems, and methods are not limited to the specific embodiments described herein, but rather, components of the apparatus, systems, and/or steps of the method may be utilized independently and separately from other components and/or steps described herein. For example, the apparatus may also be used in combination with other systems and methods, and is not limited to practice with only a system as described herein. Rather, the exemplary embodiment can be implemented and utilized in connection with many other systems.

Although specific features of various embodiments of the invention may be shown in some drawings and not in others, this is for convenience only. In accordance with the principles of the invention, any feature of a drawing may be referenced and/or claimed in combination with any feature of any other drawing.

This written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal language of the claims.

What is claimed is:

1. A terahertz generating assembly comprising:
a light emitting device configured to generate at least one pulsed light beam;
a first dispersion member positioned proximate to said light emitting device, wherein said first dispersion member is configured to facilitate a temporal dispersion of the at least one pulsed light beam;
a second dispersion member positioned proximate to said first dispersion member and to said light emitting device, wherein said second dispersion member is configured to facilitate a spatial dispersion of the at least one pulsed light beam;
a lens positioned proximate to each of said first and second dispersion members, wherein said lens is configured to focus the temporal and spatial dispersions of the at least one pulsed light beam to produce at least one moving spot of light; and
at least one waveguide positioned proximate to said lens, wherein said at least one waveguide is configured to apply a biased voltage to the at least one moving spot of light to generate pulsed terahertz radiation.

2. A terahertz generating assembly in accordance with claim 1, further comprising a pulse shaper positioned proximate to said first dispersion member, wherein said pulse shaper is configured to control a pulse shape of the at least one pulsed light beam.

3. A terahertz generating assembly in accordance with claim 2, wherein said pulse shaper is further configured to change at least one of a delay and an attenuation of a wavelength of the at least one pulsed light beam.

4. A terahertz generating assembly in accordance with claim 1, further comprising an amplifier configured to amplify the at least one pulsed light beam.

5. A terahertz generating assembly in accordance with claim 1, further comprising a substrate member positioned proximate to said lens such that said substrate member receives the at least one moving spot of light, wherein said substrate member is fabricated from a semiconducting material.

6. A terahertz generating assembly in accordance with claim 5, wherein said at least one waveguide comprises a first waveguide and a second waveguide that are each coupled to said substrate member such that said first waveguide is positioned a predefined distance from said second waveguide.

7. A terahertz generating assembly in accordance with claim 6, wherein said first waveguide is configured to apply the biased voltage on said substrate member to facilitate the generation of the pulsed terahertz radiation and said second waveguide is configured to provide an output terminal for the pulsed terahertz radiation.

8. A system comprising:
an antenna; and
a terahertz generating assembly coupled to said antenna, wherein said terahertz generating assembly comprises:
a light emitting device configured to generate at least one pulsed light beam;
a first dispersion member positioned proximate to said light emitting device, wherein said first dispersion member is configured to facilitate a temporal dispersion of the at least one pulsed light beam;
a second dispersion member positioned proximate to said first dispersion member and to said light emitting device, wherein said second dispersion member is configured to facilitate a spatial dispersion of the at least one pulsed light beam;
a lens positioned proximate to each of said first and second dispersion members, wherein said lens is configured to focus the temporal and spatial dispersions of the at least one pulsed light beam to produce at least one moving spot of light; and
at least one waveguide positioned proximate to said lens, wherein said at least one waveguide is configured to apply a biased voltage to the at least one moving spot of light to generate pulsed terahertz radiation.

9. A system in accordance with claim 8, wherein said terahertz generating assembly further comprises a pulse shaper positioned proximate to said first dispersion member, wherein said pulse shaper is configured to control a pulse shape of the at least one pulsed light beam.

10. A system in accordance with claim 9, wherein said pulse shaper is further configured to change at least one of a delay and an attenuation of a wavelength of the at least one pulsed light beam.

11. A system in accordance with claim 8, wherein said terahertz generating assembly further comprises an amplifier configured to amplify the at least one pulsed light beam.

12. A system in accordance with claim 8, wherein said terahertz generating assembly further comprises a substrate member positioned proximate to said lens such that said substrate member receives the at least one moving spot of light, wherein said substrate member is fabricated from a semiconducting material.

13. A system in accordance with claim 12, wherein said at least one waveguide comprises a first waveguide and a second waveguide that are each coupled to said substrate member such that said first waveguide is positioned a predefined distance from said second waveguide.

14. A system in accordance with claim 13, wherein said first waveguide is configured to apply the biased voltage on said substrate member to facilitate the generation of the pulsed terahertz radiation and said second waveguide is configured to provide an output terminal for the pulsed terahertz radiation.

15. A method of generating pulsed terahertz radiation, said method comprising:
generating at least one pulsed light beam via a light emitting device;
providing a temporal dispersion of the at least one pulsed light beam via a first dispersion member that is positioned proximate to the light emitting device;
providing a spatial dispersion of the at least one pulsed light beam via a second dispersion member that is positioned proximate to the first dispersion member and to the light emitting device;
focusing the temporal and spatial dispersions of the at least one pulsed light beam, via a lens positioned proximate to each of the first and second dispersion members, to produce at least one moving spot of light; and
applying a biased voltage to the at least one moving spot of light, via a first waveguide that is positioned proximate to the lens, to generate pulsed terahertz radiation.

16. A method in accordance with claim 15, further comprising:
controlling at least one of a pulse shape of the at least one pulsed light beam via a pulse shaper.

17. A method in accordance with claim 16, further comprising:
controlling at least one of a delay and an attenuation of a wavelength of the at least one pulsed light beam via the pulse shaper.

18. A method in accordance with claim 15, further comprising amplifying the at least one pulsed light beam via an amplifier.

19. A method in accordance with claim 15, further comprising receiving the moving spot of light via a substrate member that is positioned proximate to the lens, wherein the substrate member is fabricated from a semiconducting material.

20. A method in accordance with claim 19, further comprises applying the biased voltage on the substrate member, via the first waveguide, to facilitate the generation of the pulsed terahertz radiation.

21. A method in accordance with claim 20, further comprising providing an output terminal for the pulsed terahertz radiation via a second waveguide that is coupled to the substrate member such that the second waveguide is positioned a predefined distance from the first waveguide.

* * * * *